United States Patent
Ay et al.

(10) Patent No.: US 9,986,960 B2
(45) Date of Patent: Jun. 5, 2018

(54) ROBOTIC SYSTEM FOR SPECT IMAGING

(71) Applicant: PARTO NEGAR PERSIA CO., Tehran OT (IR)

(72) Inventors: Mohammad Reza Ay, Tehran (IR); Mohammad Hossein Farahani, Tehran (IR); Saeed Sarkar, Tehran (IR); Behnoosh Teimourian Fard, Tehran (IR); Salar Sajedi Toighoun, Tehran (IR); Sanaz Kaviani, Tehran (IR)

(73) Assignee: PARTO NEGAR PERSIA CO., Tehran (IR)

( * ) Notice: Subject to any disclaimer, the term of this patent is extended or adjusted under 35 U.S.C. 154(b) by 89 days.

(21) Appl. No.: 15/099,015

(22) Filed: Apr. 14, 2016

(65) Prior Publication Data

US 2016/0220204 A1    Aug. 4, 2016

Related U.S. Application Data

(60) Provisional application No. 62/164,584, filed on May 21, 2015.

(51) Int. Cl.
*A61B 6/00* (2006.01)
*A61B 6/03* (2006.01)

(52) U.S. Cl.
CPC ......... *A61B 6/4458* (2013.01); *A61B 6/037* (2013.01); *A61B 6/4266* (2013.01); *A61B 6/54* (2013.01)

(58) Field of Classification Search
CPC ..... A61B 6/4458; A61B 6/037; A61B 6/4266; A61B 6/54
See application file for complete search history.

(56) References Cited

U.S. PATENT DOCUMENTS

| | | | |
|---|---|---|---|
| 5,349,190 A | 9/1994 | Hines et al. | |
| 5,779,209 A | 7/1998 | Johnston | |
| 6,150,662 A | 11/2000 | Hug et al. | |
| 6,288,397 B1 * | 9/2001 | Maor | G01T 1/1642 250/363.04 |
| 6,577,890 B1 | 6/2003 | Hayes et al. | |
| 7,676,255 B2 * | 3/2010 | Wang | A61B 6/04 5/600 |
| 8,160,205 B2 | 4/2012 | Saracen et al. | |
| 8,252,049 B2 * | 8/2012 | Maschke | A61B 6/12 606/108 |
| 8,310,468 B2 | 11/2012 | Martin | |
| 8,452,381 B2 | 5/2013 | Cora et al. | |
| 2004/0176676 A1 * | 9/2004 | Graw | A61B 6/04 600/407 |
| 2008/0135768 A1 * | 6/2008 | Chang | G01T 1/1642 250/363.04 |

(Continued)

*Primary Examiner* — Christine Sung
(74) *Attorney, Agent, or Firm* — NovoTechIP International PLLC

(57) ABSTRACT

A robotic arm, movable in three rotational degrees of freedom has a base end and a distal end supporting SPECT imaging detectors. A patient support assembly is movable in a linear degree of freedom. A controller causes the robotic arm to move the SPECT imaging detectors, in three dimensions, around the patient's body to obtain SPECT images. The control causes the patient support assembly to move along the linear degree of freedom, maintaining alignment of the patient's body with the SPECT imaging detectors.

16 Claims, 15 Drawing Sheets

(56) References Cited

U.S. PATENT DOCUMENTS

| | | | |
|---|---|---|---|
| 2008/0137806 A1* | 6/2008 | Chang | A61B 6/037 378/17 |
| 2009/0057560 A1* | 3/2009 | Ray | G01T 1/1648 250/363.04 |
| 2009/0088621 A1* | 4/2009 | Xu | A61B 6/032 600/407 |
| 2009/0140152 A1* | 6/2009 | Zakrzewski | G01T 1/166 250/363.05 |
| 2010/0046817 A1* | 2/2010 | Goedicke | A61B 6/503 382/131 |
| 2010/0163694 A1 | 7/2010 | Fadler | |
| 2013/0261446 A1* | 10/2013 | Paladini | A61B 5/0064 600/436 |
| 2013/0320234 A1* | 12/2013 | Volokh | A61B 6/037 250/453.11 |
| 2017/0172527 A1* | 6/2017 | Uber, III | A61B 6/481 |

\* cited by examiner

ROBOTIC SYSTEM FOR SPECT IMAGING

CROSS REFERENCE TO RELATED APPLICATION

This application claims the benefit of priority from U.S. Provisional Patent Application Ser. No. 62/164,584, filed on May 21, 2015, and entitled "CARDIAC SPECT IMAGING USING ROBOTICS ARM MOVEMENTS," which is incorporated by reference herein in its entirety.

TECHNICAL FIELD

The present application generally relates to single photon emission computed tomography (hereinafter "SPECT") imaging, and particularly to a robotic system and apparatus for dedicated SPECT imaging, and more particularly to a robotic system for dedicated cardiac SPECT imaging.

BACKGROUND

SPECT imaging is a nuclear imaging technique using gamma rays, which can be utilized to track the distribution of a radionuclide inside a patient's body. SPECT imaging involves injecting a radiopharmaceutical into a patient's blood stream prior to the scan. The radiopharmaceuticals attach themselves to the target organ or specific cells. The injected radiopharmaceuticals emit radiation photons, which are detectable by a SPECT imaging device. The SPECT imaging shows how the injected radiopharmaceuticals are distributed in the patient's body. This distribution pattern can be used to understand how well the organs and tissues are functioning.

Conventional SPECT systems can include a gantry containing one or multiple SPECT imaging detectors, rotatable around the patient's body to generate images of gamma ray emission of the regional distribution of the radiopharmaceuticals. To achieve higher quality images, the SPECT imaging detectors must be positioned and moved very close to the patient's body. Generally, the SPECT imaging detectors are rotated in a stepwise manner around a patient's body contour, with successive adjustments in the radial and lateral position of the detectors.

There is a need in the art for a SPECT imaging apparatus that can provide stable, movable support for SPECT imaging detectors very close to a patient's body to obtain, for example, higher quality images. There is also a need in the art for a simple, durable design for a SPECT imaging apparatus.

SUMMARY

The following brief summary is not intended to include all features and aspects of the present application, nor does it imply that the application must include all features and aspects discussed in this summary.

The instant application discloses various systems and apparatuses directed to SPECT imaging. Various exemplary apparatuses are disclosed, and examples can include a robotic arm movable in three rotational degrees of freedom, comprising a base end and a distal end. The distal end can be configured to support a plurality of SPECT imaging detectors. In an aspect, an exemplary apparatus can include a patient support assembly, movable in a linear degree of freedom, and a controller. In an aspect, the controller can be configured to cause the robotic arm to move the plurality of SPECT imaging detectors, in three dimensions, around a patient's body to obtain SPECT images, and can cause the patient support assembly to move along the linear degree of freedom, to maintain alignment of the patient's body with the plurality of SPECT imaging detectors.

In an aspect, the three rotational degrees of freedom can include a first roll axis, a second roll axis and a third roll axis. The robotic arm can include a first arm assembly having a first rotational mechanism coupled with a proximal end of a second arm, and the first rotational mechanism can be configured to drive a roll-rotation movement of the second arm along the second roll axis. In another aspect, a base assembly having a base rotational mechanism can be coupled with the first arm assembly, and can be configured to drive a roll-rotation movement of the first arm assembly along the first roll axis. In an aspect, the head assembly can include a head rotational mechanism that can be configured to drive a roll-rotation movement of the head assembly along the third roll axis.

In an aspect, the head assembly can include a plurality of detector housings, and the plurality of detector housings can be configured to hold the plurality of SPECT imaging detectors. In another aspect, the roll-rotation movement of the second arm along the second roll axis can be configured, for example, in a rotational range of about 70 degrees. The roll-rotation of the head assembly along the third roll axis, in another aspect, can be configured in a rotational range, for example, of about 50 degrees.

Exemplary structure of the base rotational mechanism, in an aspect, can include a base motor coupled to a base shaft, and the base motor and the base shaft can be configured to drive the roll-rotation movement of the first arm assembly along the first roll axis. The first rotational mechanism can include, according to an aspect, a first motor coupled to a first shaft, and the first motor and the first shaft can be configured to drive the roll-rotation movement of the second arm along the second roll axis. Exemplary structure of the first rotational mechanism can include a first motor coupled to a first shaft, the first motor and the first shaft being configured to drive the roll-rotation movement of the second arm along the second roll axis. In an aspect, the head rotational mechanism can include a head motor coupled to a head shaft, and the head motor and the head shaft can be configured to drive the roll-rotation movement of the head assembly along the third roll axis.

In an aspect, the first roll axis, the second roll axis, the third roll axis can be parallel. In another aspect, the degree of linear freedom can be along a linear axis, and the linear axis can be parallel to the first roll axis, the second roll axis, and the third roll axis. Exemplary structure of the base rotational mechanism can include an encoder coupled to the base rotational mechanism and configured to detect the position and movement of the base shaft along the first roll axis, and to send to the controller the detected position and movement of the base shaft along the first roll axis. Exemplary structure of the first rotational mechanism can also include an absolute encoder coupled to the first rotational mechanism and configured to detect the position and movement of the first shaft along the second roll axis. In another aspect, exemplary structure of the head rotational mechanism can include an absolute encoder coupled to the head rotational mechanism. The absolute encoder can be configured, in one aspect, to detect the position and movement of the head shaft along the third roll axis, and to send to the controller the detected position and movement of the base shaft along the first roll axis.

In an aspect, the linear degree of motion can be along a linear axis, and the patient support assembly can include a moving mechanism, and the moving mechanism can be configured to move the patient support assembly along the linear axis. Exemplary structure of the moving mechanism can include, according to an aspect, a linear actuating mechanism, and the linear actuating mechanism can be configured to drive a translational movement of the patient support assembly along the linear axis. Exemplary structure of the linear actuating mechanism can include a bed motor and a bed ball screw mechanism. Exemplary structure of the patient support assembly can include a bed having a bed structure and, supported on the bed structure, a bed pad.

One exemplary apparatus is disclosed that can include the robotic arm, the patient support assembly, and the controller identified above, and can further include a sensor system that can be configured to detect the position of the robotic arm and the patient support assembly, and transmit to the controller information indicating the position of the robotic arm and of the patient support assembly. In an aspect, the controller can be configured to control the robotic arm, based at least in part on the information indicating the position of the robotic arm and of the patient support assembly.

Another exemplary apparatus is disclosed that can include the robotic arm, the patient support assembly, and the controller identified above, and the robotic arm can further include a head assembly, configured to house the plurality of SPECT imaging detectors. In an aspect, the head assembly can be attached to the distal end of a second arm. In another aspect, the robotic arm can further include a first arm assembly having a first rotational mechanism coupled with the proximal end of a second arm. In an aspect, features of the structures identified above can include rotating the SPECT imaging detectors around the patient's body at a given distance, in a roll-rotation movement from a left posterior oblique to a right anterior oblique in a given rotational range. In structures configured according to one or more aspects, the rotational range can be approximately 90 degrees, and the distance can be in a range of about 18 to 48 centimeters.

Methods directed to single photon emission computed tomography (SPECT) imaging are disclosed, and example operations according to one or more aspects can include providing a plurality of SPECT imaging detectors at a distal end of a robotic arm, and positioning a patient in a field of view of the plurality of SPECT imaging detectors. In an aspect, positioning the patient can include placing the patient on a patient support assembly that is selectively movable in a linear degree of motion, and moving the patient support assembly in the linear degree of motion, to maintain alignment of a selected region on the patient's body with a field of view (FOV) of the plurality of SPECT imaging detectors.

In operations according to one or more aspects, the robotic arm can be configured to move the robotic arm using a rotational degree of freedom, and the rotational degree of freedom can have an associated roll axis. Exemplary operations can be configured such that moving the patient support assembly in the linear degree of motion moves the patient support assembly in a translational direction parallel to the associated roll axis.

In an aspect, operations in moving the robotic arm can include driving a roll-rotation movement of a first segment of the robotic arm along a first roll axis, in combination with driving a roll-rotation movement of a second segment of the robotic arm along a second roll axis, the second roll axis being parallel to the first roll axis. Operations in moving the robotic arm can further comprise rotating a head assembly that houses the plurality of SPECT imaging detectors and is attached to a distal end of the second segment of the robotic arm, along a third roll axis, the third roll axis being parallel to the first roll axis.

Additional methods directed to SPECT imaging are disclosed, and example operations according to one or more aspects can include positioning a patient on a patient support that is movable along a linear axis, rotating a first arm in a rotation along a first roll axis, the first roll axis extending through a proximal end of the first arm, rotating a second arm in a rotation along a second roll axis, the second roll axis extending parallel to the linear axis and extending through a distal end of the first arm and a proximal end of the second arm, and being parallel to the first roll axis; rotating a plurality of SPECT imaging detectors, located at a distal end of the second arm, about a third roll axis, the third roll axis being parallel to the first roll axis; and moving the patient support in the linear degree of motion, in a manner maintaining alignment of a selected region on the patient's body with a field of view (FOV) of the plurality of SPECT imaging detectors.

BRIEF DESCRIPTION OF THE DRAWINGS

While the specification concludes with claims particularly pointing out and distinctly claiming the subject matter that is regarded as forming the present application, it is believed that the application will be better understood from the following description taken in conjunction with the accompanying DRAWINGS, where like reference numerals designate like structural and other elements, in which:

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

For purposes of explanation, specific nomenclature is set forth to provide a thorough understanding of the present application. However, it will be apparent to one skilled in the art that these specific details are not required to practice the application. Descriptions of specific applications are provided only as representative examples. Various modifications to the preferred implementations will be readily apparent to one skilled in the art, and the general principles defined herein may be applied to other implementations and applications without departing from the scope of the application. Practices according to concepts disclosed by the present application are not intended to be limited to the implementations shown, are to be accorded the widest possible scope consistent with the principles and features disclosed herein.

Disclosed systems and methods directed to SPECT imaging can include a robotic apparatus comprising a robotic arm having, as its end-effector, SPECT imaging detectors, and can include a linearly movable patient support assembly. The robotic arm, in an aspect, can be structured as movable about three rotational axes. The robotic arm, configured according to one or more aspects can provide and enable roll-rotation movement, in a three-dimensional space, of the SPECT imaging detectors around the patient's body, during SPECT imaging, while maintaining close and stably controlled spacing between the patient's body and the SPECT imaging detectors. In an aspect, the linearly movable patient support assembly can be moved along the linear axis, and the movement can be in cooperation with movement by the robotic arm of the SPECT imaging detectors. Benefits can of these features can include, but are not limited to, maintaining quality alignment between regions of interest in the patient's body and the FOV of the SPECT imaging detectors. Further benefits of the quality alignment, and the close and stably controlled spacing between the patient's body and the SPECT imaging detectors, can include, but are not limited to, higher quality SPECT images.

Figure 1:
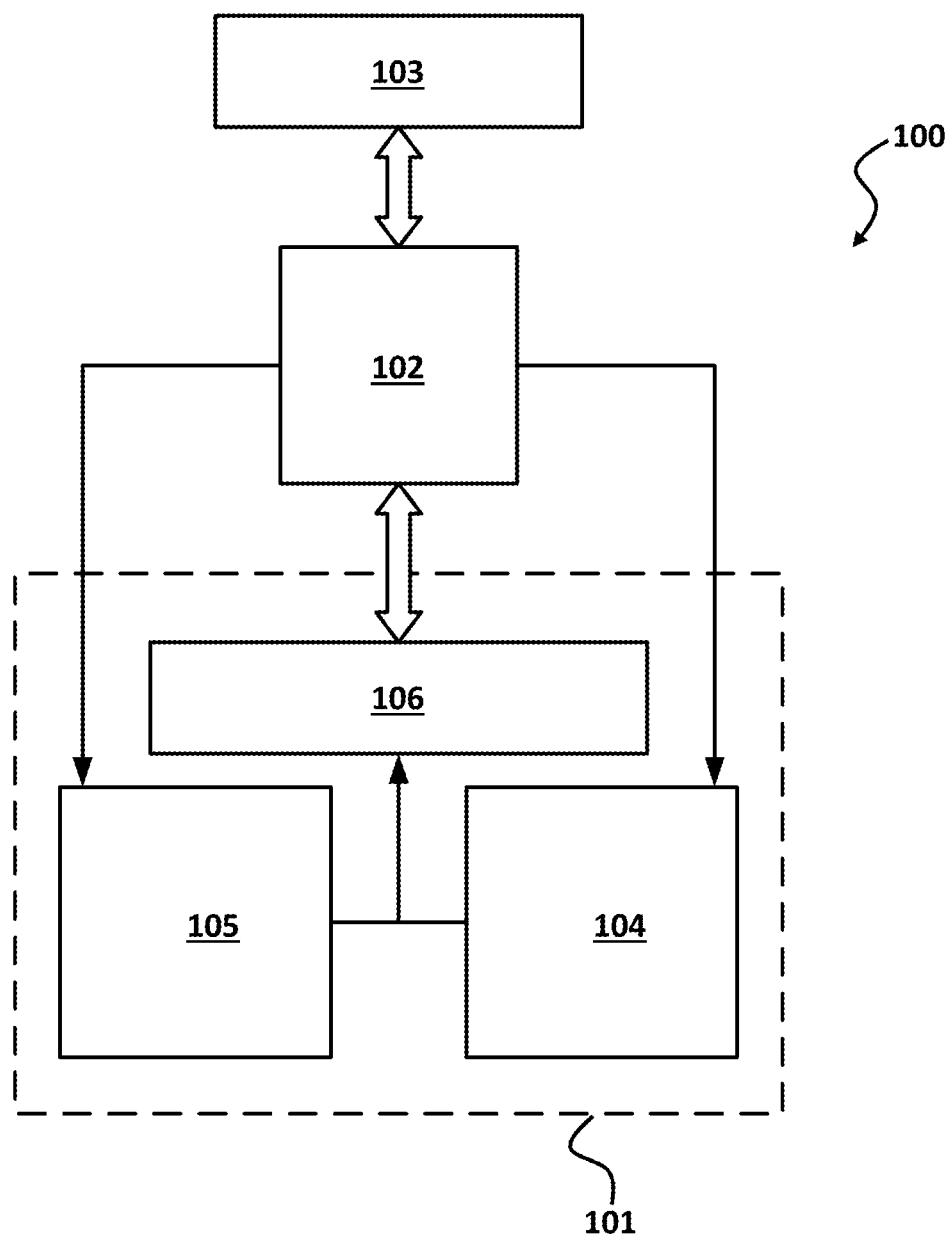
FIG. 1 illustrates a schematic block diagram of one example implementation of a robotic system for SPECT imaging, according to one or more aspects of the present application.

FIG. 1 is a schematic functional block diagram of one implementation of an example robotic system 100, directed to SPECT imaging according to one more aspects of this disclosure. The robotic system 100 can include a robotic apparatus 101, a controller 102, and a user interface unit 103. The robotic apparatus 101 can include a robotic arm 104 that can support SPECT imaging detectors (not explicitly visible in FIG. 1), as its end-effector. The robotic arm 104 can be configured, as will be described in greater detail in subsequent sections of this disclosure, to provide positioning and movement of SPECT imaging detectors using three rotational degrees of freedom. The three rotational degrees of freedom can be movement of different structures or segments, as will be described in greater detail, of the robotic arm 104 about a respective three axes of rotation.

In an aspect, the robotic system 100 can include a patient support assembly 105 configured to support and position a patient in the FOV of the SPECT imaging detectors during SPECT imaging. The patient support assembly 105 can be configured with one degree of freedom. The robotic system 100 can include a sensor system 106, configured for detecting positions and movements of the robotic arm 104 and of the patient support assembly 105. The sensor system 106 can be configured to detect such positions and movements relative to a predefined coordinate system, at any time during SPECT imaging.

The controller 102 can be coupled to the robotic arm 104, the patient support assembly 105, the sensor system 106, and the user interface unit 103 through, for example, wired links (not explicitly visible in FIG. 1), wireless links (not explicitly visible in FIG. 1), or a combination of wired and wireless links. The controller 102 can be configured to control the position and the motion of the robotic arm 104 and can also be configured to control the patient support assembly 105. The controller 102 can be operatively coupled to the sensor system 106 and to the user interface unit 103 of the robotic system 100, for purposes that can include calculating the position and the motion of the robotic arm 104 and the patient support assembly 105 during SPECT imaging. The calculating of the position and the motion of the robotic arm 104 and the patient support assembly 105 can be based, at least in part, on data received from a user through the user interface unit 103, or data received from the sensor system 106, or both. In an aspect, the controller 102 can also be configured to control position and motion of the SPECT imaging detectors around and near a patient's body, during SPECT imaging.

The sensor system 106 can include position feedback encoders (not explicitly visible in FIG. 1), which can be coupled to motors (not explicitly visible in FIG. 1) that move the robotic arm 104 and the patient support assembly 105. The position feedback encoders can include, for example, conventional commercially available absolute or incremental encoders, or both, and can comprise conventional commercially available linear or rotary encoders, or both.

The user interface unit 103 can provide means for receiving data input from a user. One example implementation of the user interface unit 103 can include, for example, a graphical user interface (GUI) unit. The user interface unit 103, in combination with the controller 102, can provide means for a user to interactively control the motions of the robotic system 100 for SPECT imaging. Data input by the user can include, for example, scanning parameters. The term "scanning parameters," as used herein, can include an angle and a radius of a scanning arc. The term "scanning arc," as used herein, means the path in three-dimensional aspect, in which the SPECT imaging detectors move around the patient's body contour. The angle of the scanning arc determines the rotational range of the roll-rotation movement of the SPECT imaging detectors around the patient's body and the radius of the scanning arc, determines the distance between the detectors and the patient's body during SPECT imaging.

The controller 102 can be configured with a memory (not explicitly visible in FIG. 1) for include executable instructions that, when executed, cause the controller 102 to perform operations further to processes and methods disclosed herein. Such operations can include, for example, conversion of the position and the movement data received from the sensor system 106, and from the user interface unit 103, to appropriate units along the three axes of rotation in which the robotic arm 104 can move, and the linear axis provided by patient support assembly 105.

Figure 2A:
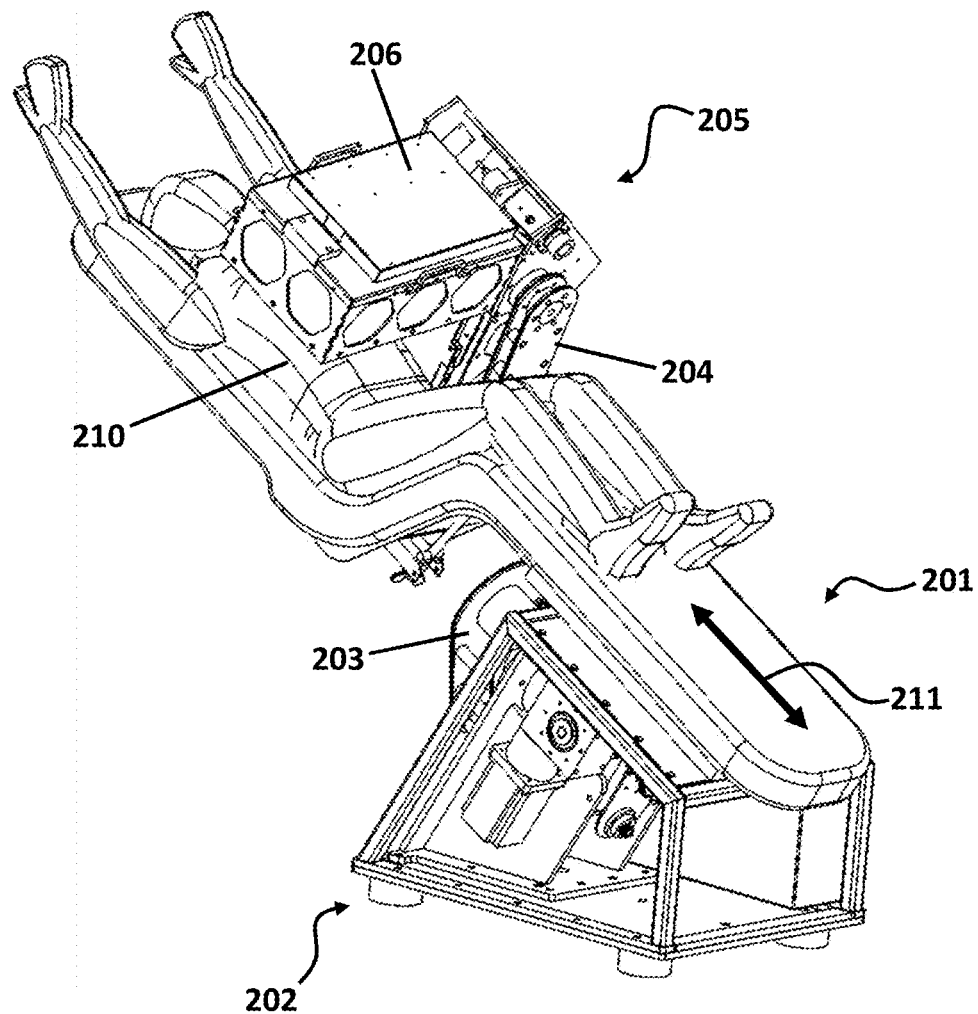
FIG. 2A illustrates one implementation of an example robotic arm for one robotic system for SPECT imaging, according to one or more aspects of the present application.
Figure 2B:
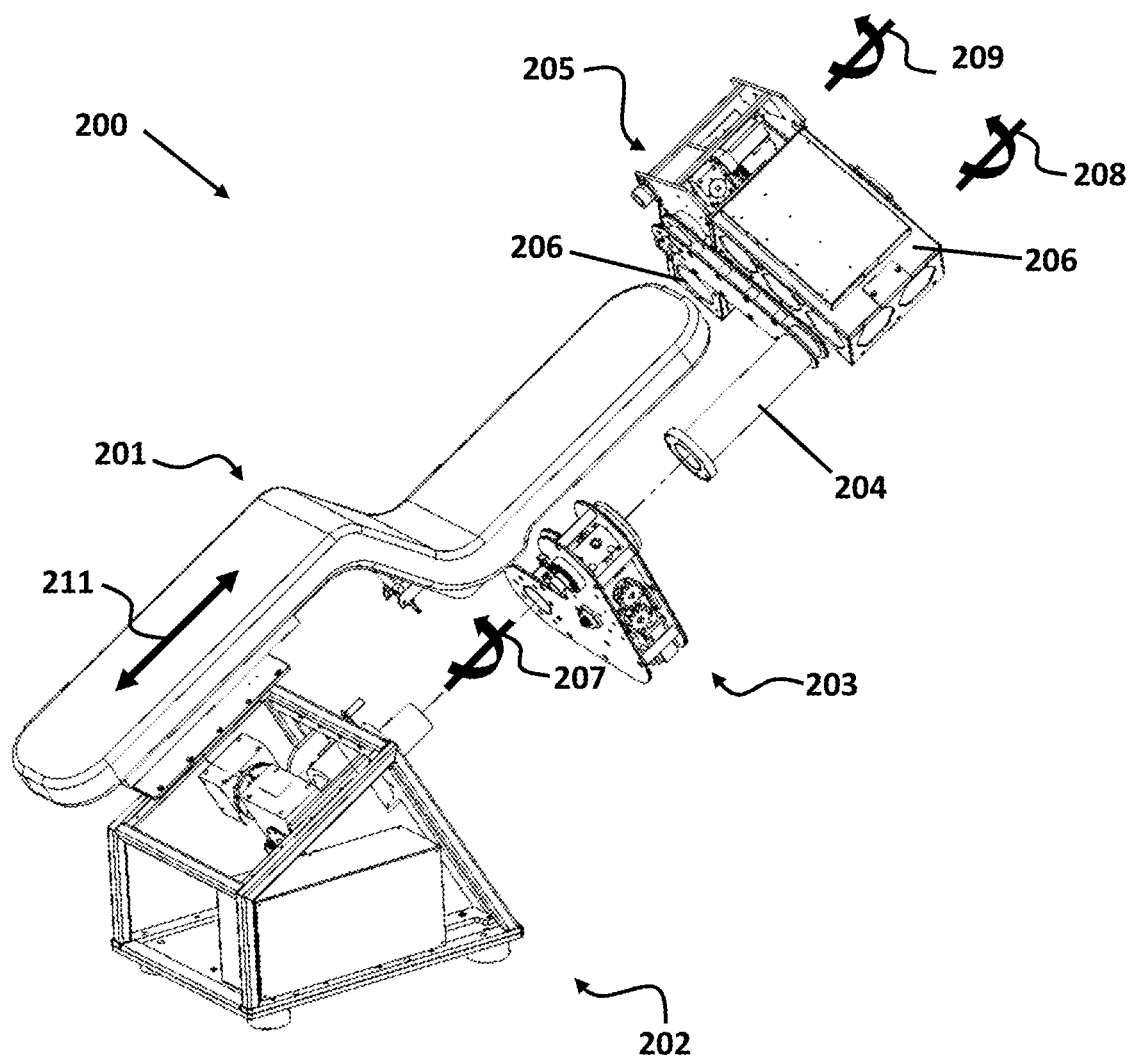
FIG. 2B illustrates an exploded view of one implementation of an example robotic apparatus, for a system for SPECT imaging according to one or more aspects of the present application.

FIG. 2A shows an exploded view of one example robotic SPEC imaging apparatus 200 configured to provide an example implementation of the FIG. 1 robotic system 100. FIG. 2B shows an assembled view of the robotic SPEC imaging apparatus 200, with a patient 210.

Referring to FIG. 2A, the SPEC imaging apparatus 200 can include a base assembly 202, a first arm assembly 203, a second arm 204, and a head assembly 205. The second arm 204 can be alternatively referred to as "middle arm 204." The head assembly 205 can have a plurality, for example two, detector housings 206, inside of which the SPECT imaging detectors (not explicitly visible in the figures) can be placed.

Referring to FIG. 2A, the SPEC imaging apparatus 200 can include a patient support assembly 201, which may be structured as a bed or a treatment table, configured to support a patient, such as the example patient 210 shown in FIG. 2B, during SPECT imaging. The patient support assembly 201 can include a moving mechanism, as described in greater detail later in this disclosure, to effectuate movement of the patient support assembly 201 along a linear axis 211.

The base assembly 202 can be coupled with the first arm assembly 203. The base assembly 202 can be configured with a base rotational mechanism (visible in FIGS. 2A and 2B, but not separately numbered) to drive rotational movement of the first arm assembly 203 along a first roll axis 207. One example of a base rotational mechanism can be the base rotational mechanism 213 described in greater detail in reference to FIG. 2E.

The first arm assembly 203 can be coupled with the proximal end (visible as a flange-shaped structure, but not separately labeled) of the second arm 204. Referring to FIG. 2G, the first arm assembly 203 can include a first rotational mechanism 220, described later in greater detail. In an aspect, the proximal end of the second arm 204 can be coupled to the first rotational mechanism 220 of the first arm assembly 203 and the distal end of the second arm 204 (visible but not separately numbered) can be coupled to the head assembly 205. The first rotational mechanism 220 can be configured to drive rotational movement of the second arm 204 along a second roll axis 208. In the described structure, rotational movement of the second arm 204 along the second roll axis 208 can impart rotational movement of the head assembly 205 in a roll-rotation along the second roll axis 208.

The head assembly 205 can include a head rotational mechanism (not explicitly visible in the figures), configured to drive rotational movement of the head assembly 205, and the SPECT imaging detectors in its exemplary detector housings 206, along a third roll axis 209.

Figure 2C:
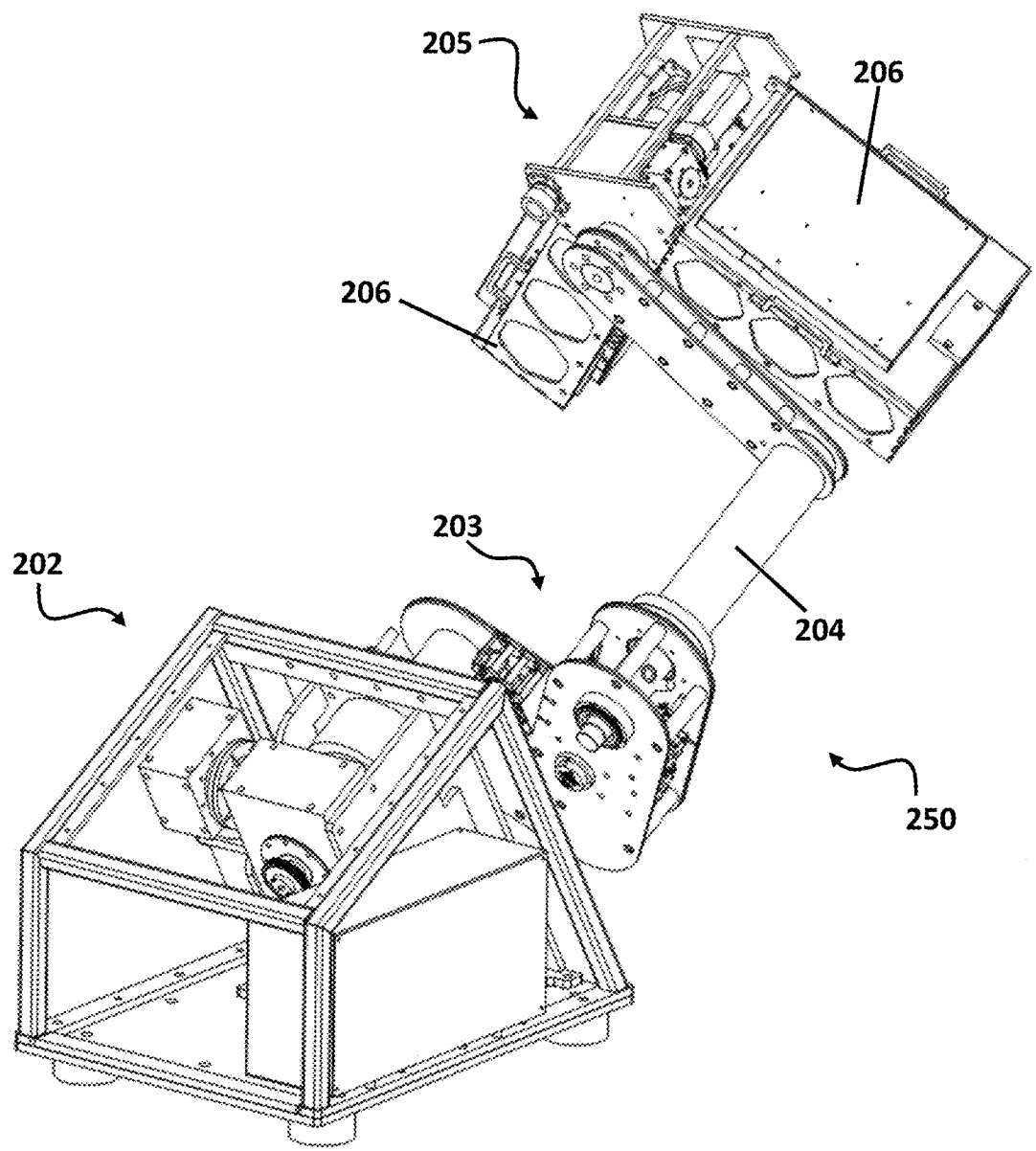
FIG. 2C illustrates a perspective view of one implementation of an example robotic apparatus, for a system for SPECT imaging according to one or more aspects of the present application.

Referring to FIG. 2C, for purposes of description, the first arm assembly 203 and second arm 204 are collectively referenced as "robotic arm 250," as labeled on the figure. Also for purposes of description, the first arm assembly 203 can be alternatively referenced as the "first arm segment" of the robotic arm 250, and the second arm 204 can be alternatively referenced as the "second arm segment."

In an aspect, the first roll axis 207, the second roll axis 208, the third roll axis 209, and the linear axis 211 can be mutually parallel. The robotic arm 200 with three rotational degrees of freedom, namely, along the first roll axis 207, the second roll axis 208, and the third 209 roll axes, can move SPECT imaging detectors in a three dimensional space, as well as roll-rotation of the SPECT imaging detectors around the first roll axis 207 around and near a patient's body. The patient support assembly 201 with one degree of freedom along the linear axis 211 can provide positioning of a patient 210 in the FOV of the SPECT imaging detectors attached to the robotic arm 200.

Figure 2D:
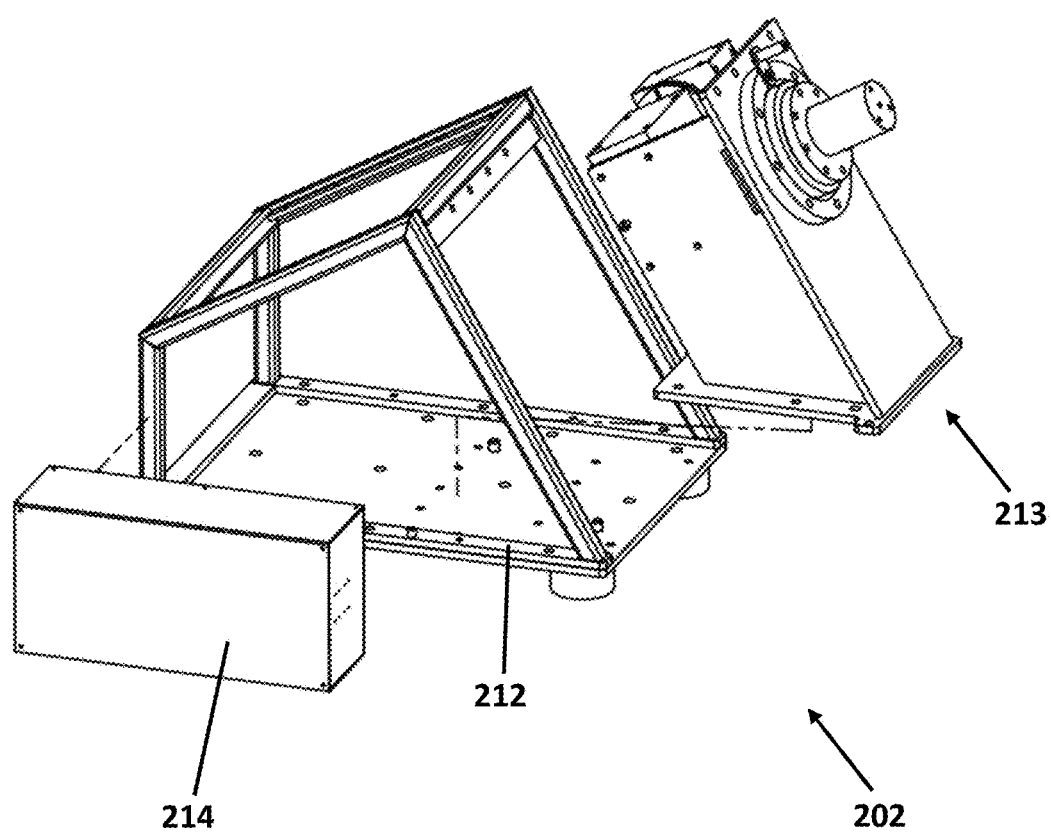
FIG. 2D illustrates one implementation of an example base assembly for a robotic apparatus, for a system for SPECT imaging according to one or more aspects of the present application.
Figure 2E:
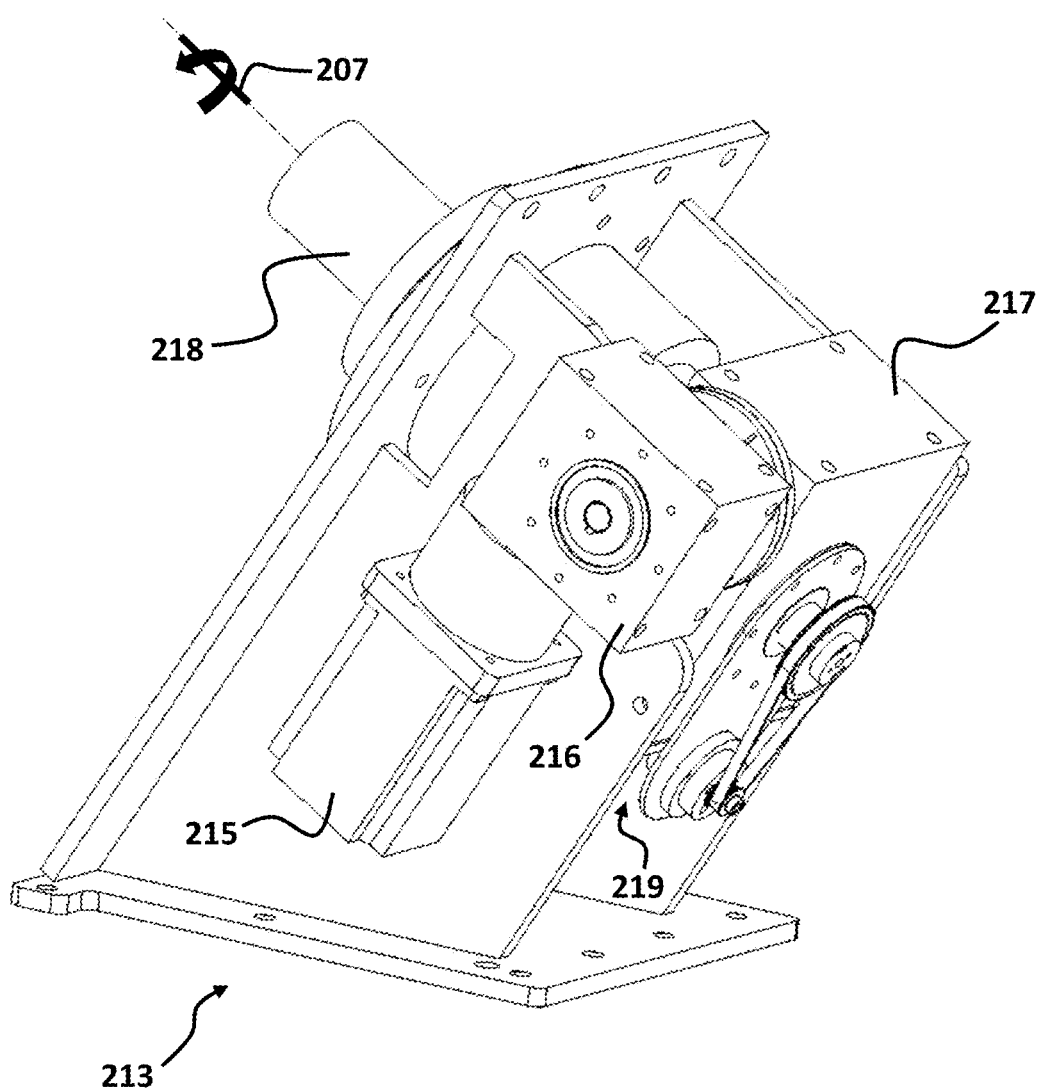
FIG. 2E illustrates an implementation of an example base rotational mechanism for a robotic apparatus, for a system for SPECT imaging according to one or more aspects of the present application.
Figure 2F:
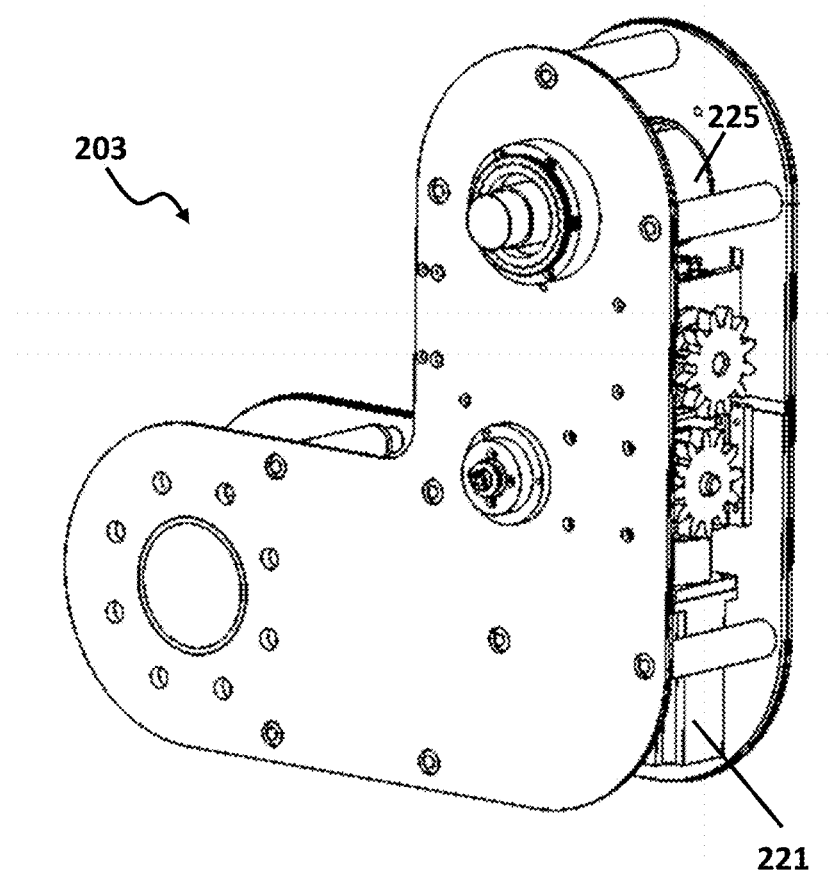
FIG. 2F illustrates one implementation of an example first arm assembly, of one exemplary robotic arm, for a system for SPECT imaging according to one or more aspects of the present application.
Figure 2G:
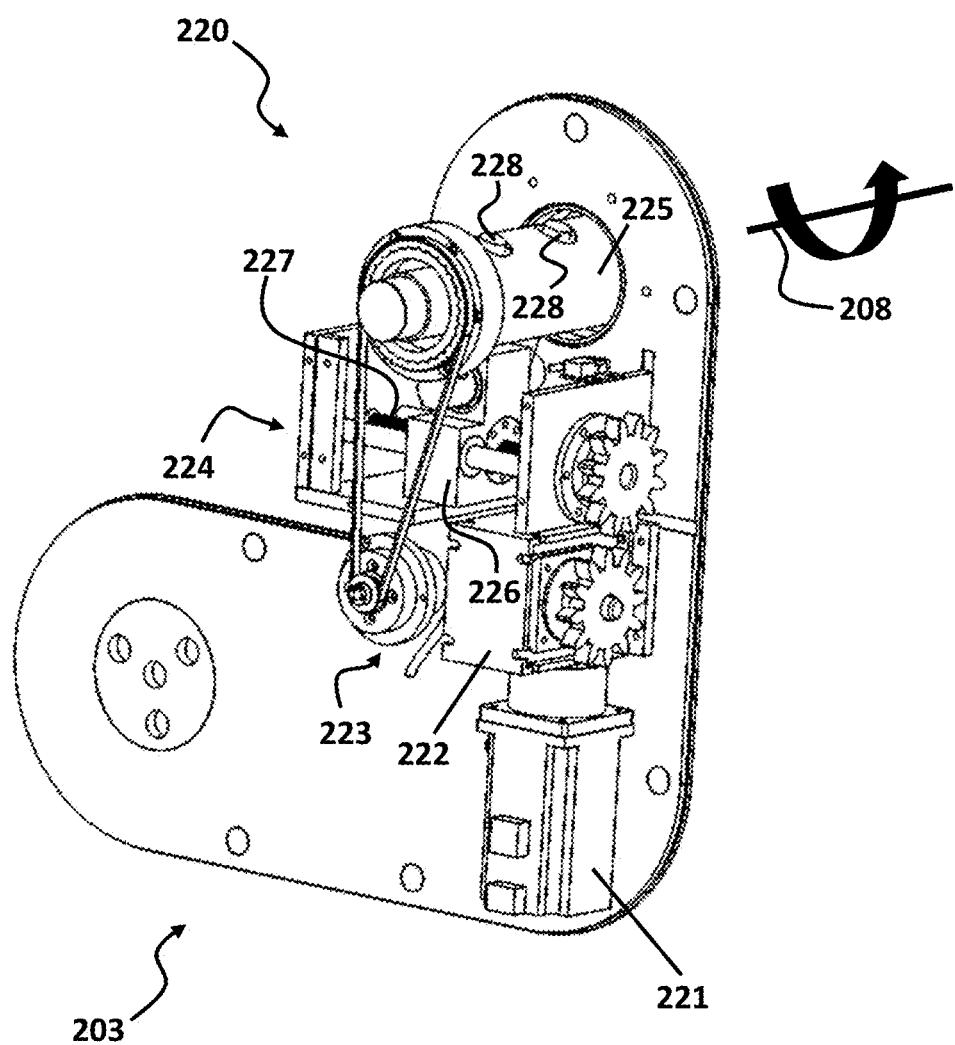
FIG. 2G illustrates one implementation of an example first rotational mechanism of a robotic apparatus, for a system for SPECT imaging according to one or more aspects of the present application.
Figure 2H:
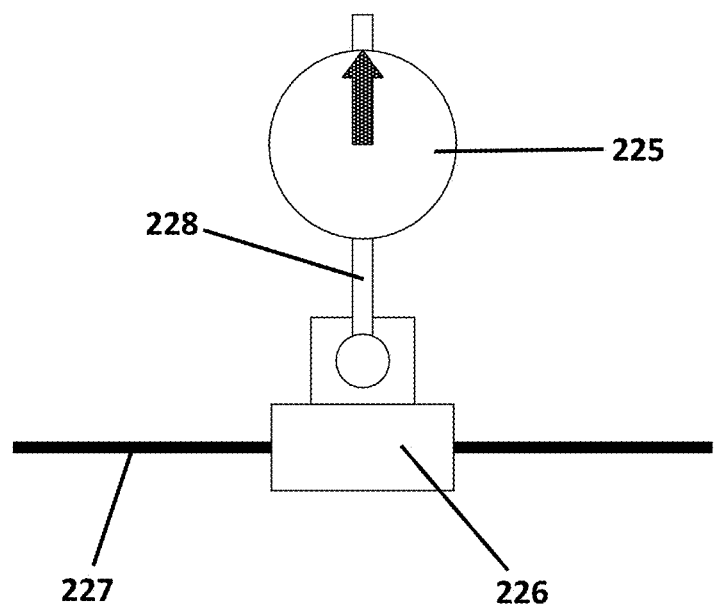
FIGS. 2H-2I illustrate aspects of one exemplary first ball screw mechanism of a robotic apparatus, for a system for SPECT imaging according to one or more aspects of the present application.
Figure 2I:
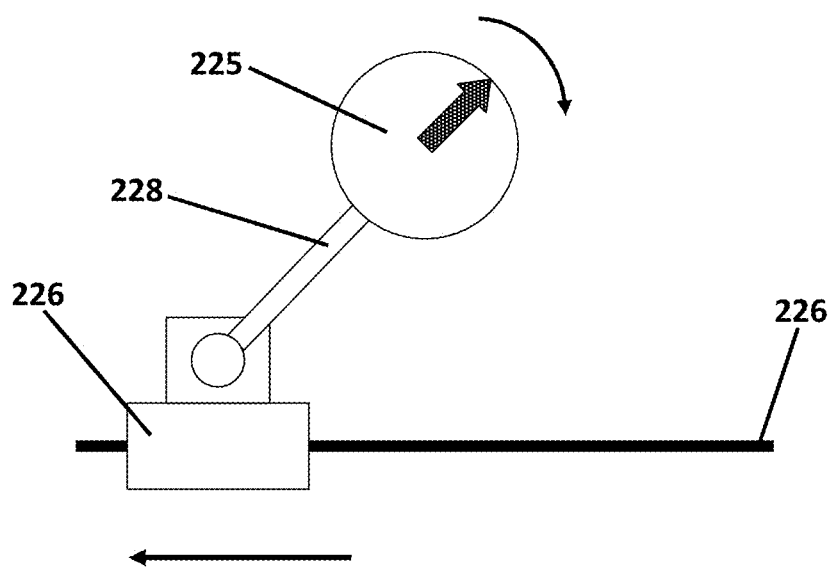
Figure 2J:
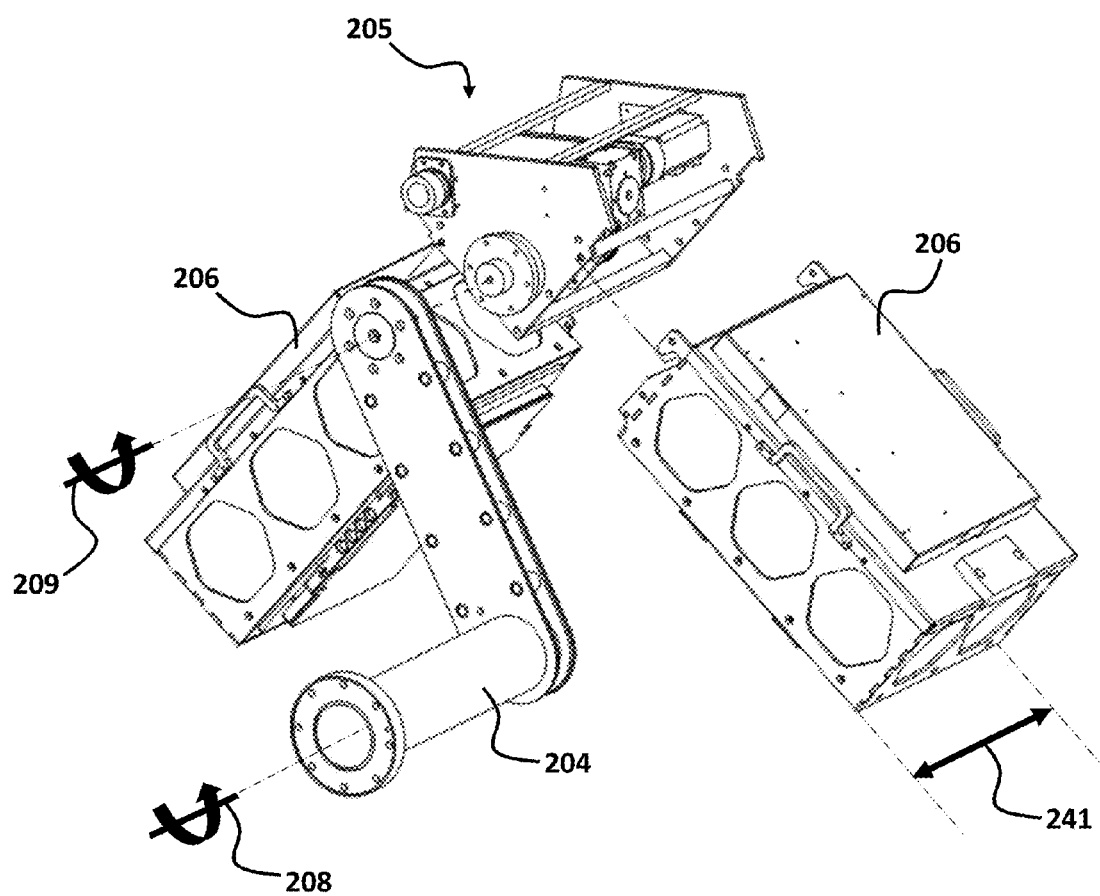
FIG. 2J illustrates an exploded view of one implementation of one example second arm and head assembly of a robotic arm in one robotic apparatus, for a system for SPECT imaging according to one or more aspects of the present application.

Referring to FIG. 2J, each detector housing 206 attached to the head assembly 205 has a width 241. As used in this application, the recitation "positioning of a patient in the FOV of the SPECT imaging detectors" means positioning the patient under the SPECT imaging detectors such that the part of the patient's body that is the target of the SPECT imaging can be placed in the middle—in a widthwise sense—of the SPECT imaging detectors. As one illustration, operations according to one implementation can be applied to cardiac SPECT imaging, and positioning of the patient in such imaging can include the patient's heart being positioned in the FOV of the SPECT imaging detectors.

Referring to FIG. 2D, in an aspect, the base assembly 202 can include a base frame 212 and, assembled on the base frame 212, a base rotational mechanism 213 and a control box 214. The base rotational mechanism 213 can be configured to drive rotational movement of the first arm assembly 203 along the first roll axis 207. The control box 214 can house, for example, a control board, an interface module, and other electronic components.

FIG. 2E shows one example base rotational mechanism 213. Referring to FIG. 2E, the base rotational mechanism 213 can include a base motor 215 and a base shaft 218. The base motor 215 can be implemented, for example, with a servo-motor or other conventional motor type such as known by persons of ordinary skill in the art. In some implementations, the base motor 215 can be coupled to the base shaft 218 through a transmission system (visible in FIG. 2E but not separately labeled). The transmission system can be configured to provide the required torque and transmission ratio. Regarding specific values of torque and of transmission ratios, persons of ordinary skill in the art, upon reading this disclosure, will understand that such values are application specific. Such persons, having possession of the present disclosure, can readily determine the values for specific applications, using conventional engineering methodologies and, therefore, further detailed description of such values is omitted. One example transmission system can include, for example, a small base gearbox 216 and a large base gearbox 217. In an example arrangement, the base motor 215 can be first coupled to a small base gearbox 216, and then the small base gearbox 216 can be coupled to the large base gearbox 217. One benefit of this arrangement is that small base gearbox 216 can tolerate lower torques but provides a variety of transmission ratios. Another benefit is that the small base gearbox 216 and large base gearbox 217 can enable a more compact base rotational mechanism 213.

With continuing reference to FIG. 2E, a base absolute encoder 219 may be connected to the transmission system to detect the position of the base shaft 218. In one example implementation, the base absolute encoder 219 can be coupled to the transmission system by a belt-and-pulley mechanism, as shown in FIG. 2E. In an aspect, the base absolute encoder 219 can be structured as a multi-turn encoder. Also, in an aspect, the base absolute encoder 219 can be a part of the sensor system 106. In an aspect, the base absolute encoder 219 can be configured to detect the rotational movement and position of the base shaft 218 and send it via an interface module to the sensor system 102.

FIGS. 2F and 2G show, respectively an outer view and a partially disassembled view of an example configuration for the first arm assembly 203. Referring to FIG. 2G, the first arm assembly 203 can include, for example, a first rotational mechanism 220. The first rotational mechanism 220 can include a first motor 221 and a first shaft 225. The first motor 221 can be implemented, for example, as a servomotor or another type of motor known by those of ordinary skill in the art. In an aspect, the first motor 221 can be coupled to a first gearbox 222. The first gearbox 222 can be coupled to a first ball screw mechanism 224 and the first gearbox 222 can be configured to drive rotational movement of the first ball screw mechanism 224.

According to one example implementation, the first ball screw mechanism 224 can include a ball screw 227, and a moving member 226 that can be connected to the first shaft 225, for example, by two pins 228. The ball screw 227 can be configured to translate the rotational movement driven by the first gearbox 222 to linear motion of the moving member 226. In the arrangement shown in FIGS. 2H and 2I, when the moving member 226 moves along a linear axis, the pins 228 can operate to roll the first shaft 225 along the second roll axis 208. It will be understood that other mechanical linear actuators known by those of ordinary skill in the art can be used instead of the first ball screw mechanism 224. In an aspect, the first rotational mechanism 220 can be configured to rotate the first shaft 225 along the second roll axis 208 within a given rotational range. For purposes of illustration, one example of the given rotation range is approximately 70 degrees. The value of 70 degrees, however, is only one example. Persons of ordinary skill, upon reading this disclosure will understand that specific values of the rotational range for the first shaft 225 along the second roll axis 208 can be, at least in part, application-specific and can also be, at least in part, design choice.

In an aspect, a first arm absolute encoder 223 can be coupled to the first shaft 225, in a configuration that provides detection of the motion and the position of the first shaft 225. One example implementation can include coupling the first arm absolute encoder 223 to the first shaft 225 by a belt-and-pulley mechanism, as shown in FIG. 2G. The first arm absolute encoder 223 can be, for example a single-turn encoder, and can be a part of the sensor system 106. In an aspect, the first arm absolute encoder 223 can be configured to detect the rotational movement and position of the first shaft 225 and send it via an interface module to the controller 102.

In an aspect, the head assembly 205 can include two detector housings 206 for placing the SPECT imaging detectors. The head assembly 205 can also include a head rotational mechanism, configured to effectuate rotational movement of the head assembly 205 along the third roll axis 209.

In one implementation, the head rotational mechanism can include: a head motor 229 and a head shaft 231. The head motor 229 can be coupled with the head shaft 231 to drive rotational movement of the head assembly 205 along the third roll axis 209. In one implementation, the head motor 229 can be a servo motor or other motors known by those of ordinary skill in the art. In some implementations, the head motor 229 can be coupled with a head gearbox 230. The head gearbox 230 can be coupled to, and further configured to drive rotational movement of a head ball screw mechanism 232. In an aspect, rotation of the head ball screw mechanism 232 will rotates the head shaft 231 along a third roll axis 209. The head rotational mechanism in the head assembly 205 can be similar to that of the first arm assembly 203. According to one implementation, the head rotational mechanism can be configured to rotate the head shaft 231 along the third roll axis 209 within a given third roll axis rotational range. For purposes of illustration, one example span for the given third roll axis rotation range can include approximately 50 degrees. The value of 50 degrees is only one example. Persons of ordinary skill, upon reading the present disclosure, will understand that the specific values of the rotational range over which the head rotational mechanism can be configured to rotate the head shaft 231 along the third roll axis 209 can be, at least in part, application-specific and can also be, at least in part, design choice.

Figure 2K:
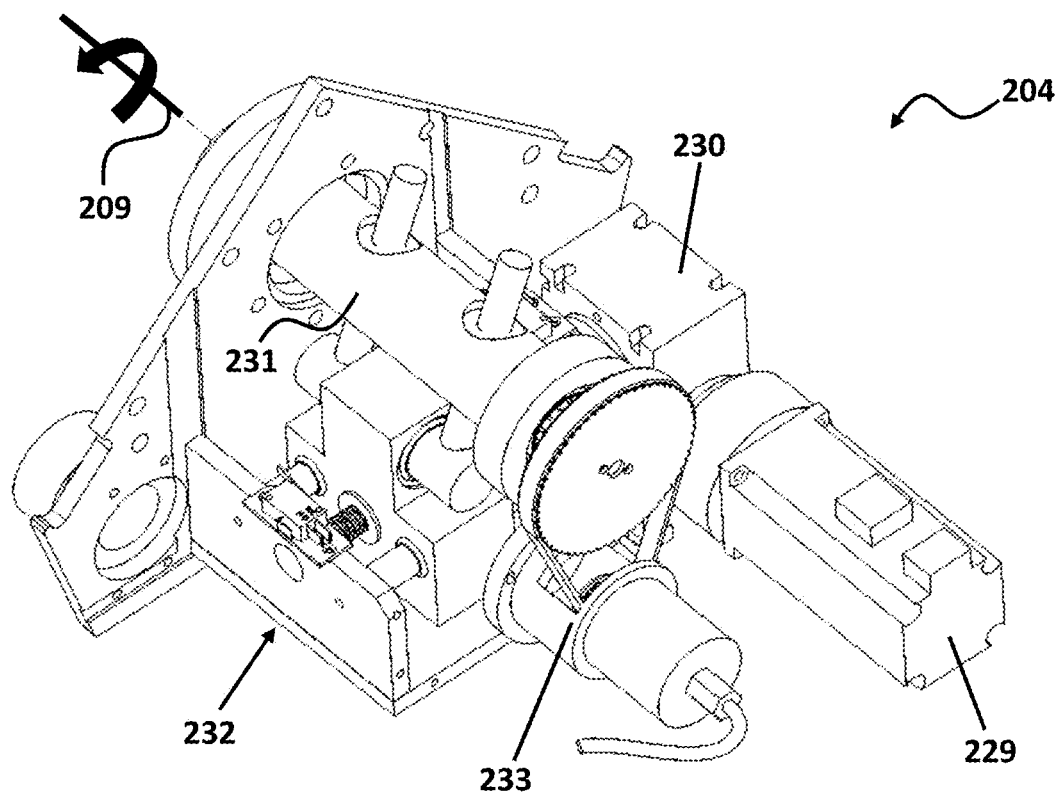
FIG. 2K illustrates one implementation of one example head rotational mechanism that can be supported by a robotic arm in a robotic apparatus, for a system for SPECT imaging according to one or more aspects of the present application.

In one implementation a head absolute encoder 233 can be coupled to the head shaft 231 in order to detect the motion and the position of the head shaft 231. In some implementations, the head absolute encoder 233 can be coupled to the head shaft 231 by a belt-and-pulley mechanism, as shown in FIG. 2K. The head absolute encoder 233 is a part of the sensor system 106. In one implementation, the head absolute encoder 233 can detect the rotational movement and position of the head shaft 231 and send it, for example, via an interface module to the controller 102.

Referring to FIG. 1 and FIGS. 2A-2M, according to one implementation, the sensor system 106 can comprise the base absolute encoder 219, the first arm absolute encoder 223 and the head absolute encoder 233. The sensor system 106 can be connected, for example, via an interface module (not explicitly visible in the figures) to the controller 102. In an aspect, the controller 102 can be configured to calculate the position and the motion of the robotic arm 104, and the patient supporting assembly 105, based on the data received from a user through the user interface unit 103 and the data received from the sensor system 106.

The patient support assembly 201 can include a bed padding 234, which can be attached to a bed structure 236. The patient support assembly 201 can be mounted on the base frame 212 of the base assembly 202, for example, by a mounting plate 235. The patient support assembly 201 has one translational degree of freedom along the linear axis 211. In an aspect, a bed moving mechanism configured, for example, as described in greater detail in paragraphs that follow, can be included to move the patient support assembly 201 along the linear axis 211.

Figure 2L:
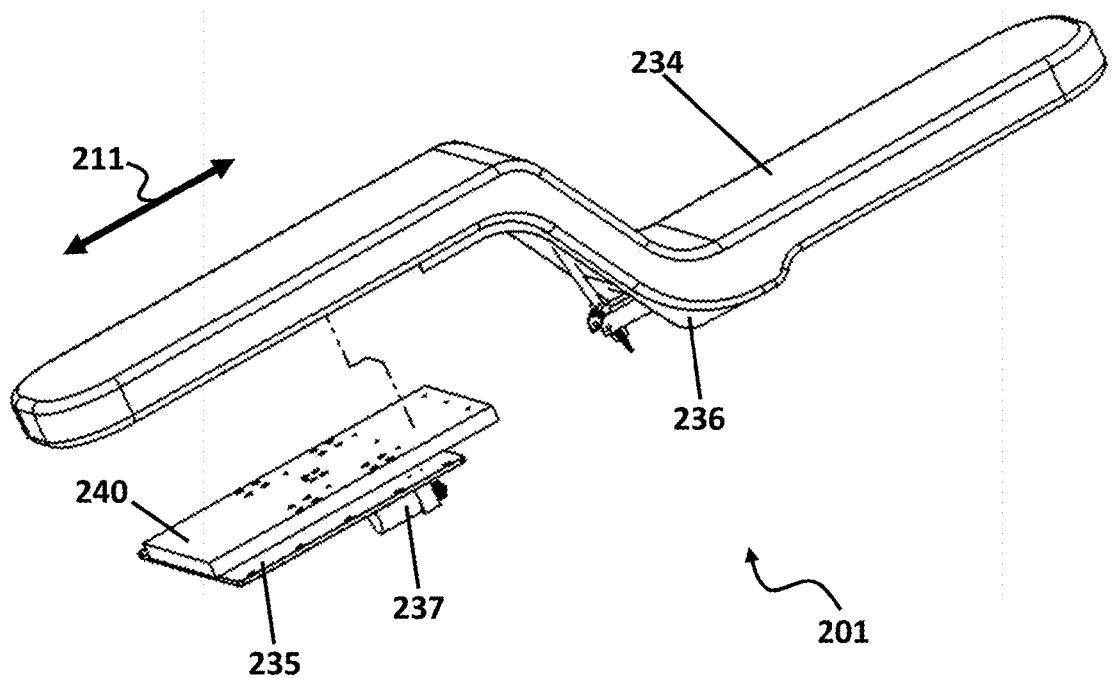
FIG. 2L illustrates one implementation of a linearly movable patient support assembly in a robotic apparatus, for a system for SPECT imaging according to one or more aspects of the present application.
Figure 2M:
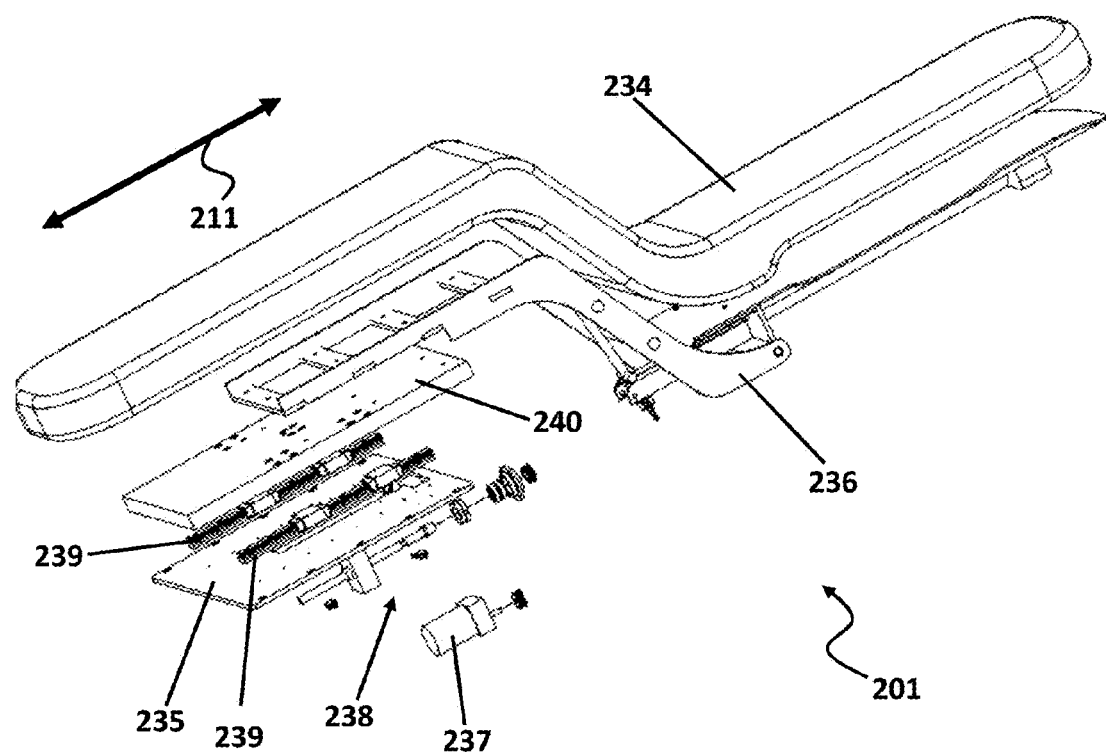
FIG. 2M illustrates an exploded view of the FIG. 2L implementation of a linearly movable patient support assembly in a robotic apparatus, for a system for SPECT imaging according to one or more aspects of the present application.

Referring to FIG. 2L bed moving mechanism (visible by its components, but not additionally labeled) can include a linear actuating mechanism constructed, for example, of a bed motor 237, a bed ball screw mechanism 238, two linear guide bars 239 and a sliding member 240 attached to the bed structure 236. The bed motor 237 can be coupled with the bed ball screw mechanism 238. The bed ball screw mechanism 238 can be configured to translate the rotational movement driven by the bed motor 237 into a linear movement along the linear axis 211. The bed motor 237 and the bed ball screw mechanism 238 can be configured to effectuate the linear movement of the sliding member 240 along the two linear guide bars 239. The sliding member 240 can be configured to slide along the two guide bars 239 and move the patient support assembly 201 in a translational movement along the linear axis 211.

In an aspect, the SPECT imaging detectors may be rotated around the patient's body by the robotic arm 250 at a distance from the patient's body in a range, for example, of about 18 to 48 centimeters. It will be understood that practices according to disclosed aspects are not limited to the example range of about 18 to 48 centimeters, and may include distances above 48 centimeters, as well as distances less than about 18 centimeters.

According to one implementation, two detector housings 206 can be attached to the head assembly 205. In an aspect, the two detector housings 206 can be orthogonal. The robotic arm 250 facilitates a roll-rotation movement of these two housings 205 along the first roll axis 207 from a starting point in a left posterior oblique to an end point in a right anterior oblique. The two detectors can be rotated in a rotational range of 90° from the left posterior oblique to the right anterior oblique, during SPECT imaging.

Once the detectors are placed in the starting point by the robotic arm 200, the translational movement of the patient support assembly 201 along the linear axis 211 can be used to position the patient's body in the FOV (FOV) of the SPECT detectors. According to one implementation in the cardiac SPECT imaging, the patient's heart is placed in the FOV of the SPECT detectors.

According to one implementation, the controller 102 can be configured to position the robotic arm 200 and the SPECT imaging detectors housed in the distal end of the robotic arm 200 in the starting point. The controller 102 can receive a current position of the robotic arm via the sensor system 106 and can then calculates the movement of the arm 200 based on the data received from the sensor system 106 and positions the robotic arm 200 in the starting point. According to another implementation, a user can manipulate the scanning parameters via the user interface unit 103.

Figure 3:
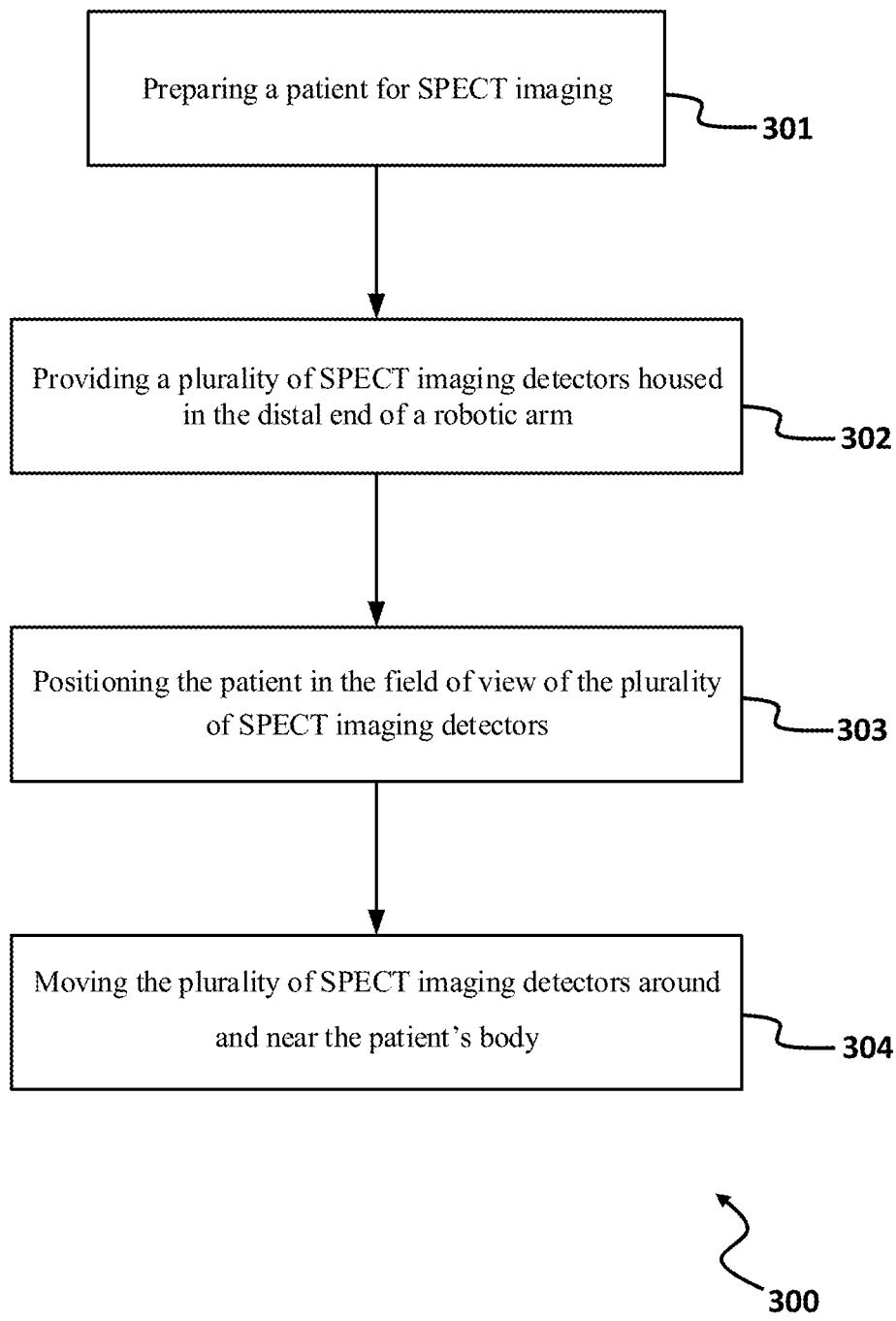
FIG. 3 illustrates a logical flow of operations in one example process in a method for SPECT imaging using a robotic assembly according to one or more aspects of the present application.

FIG. 3 is a logical flow diagram, illustrating one flow 300 of example operations within a process further to aspects of SPECT imaging using robotic apparatus of the present disclosure. Operations in the flow 300 can include preparing, at 301, a patient for SPECT imaging. Operations at 301 can be according to known techniques for patent preparation in convention SPECT and, therefore, further detailed description is omitted. The flow 300 can then proceed to 302 and provide a plurality of SPECT imaging detectors housed in the distal end of a robotic arm. Operations at 302 can include, for example, providing an apparatus such as the robotic SPEC imaging apparatus 200 described above in reference to FIGS. 2A-2M. After operations at 302, the flow can proceed to 303, and apply operations to position the patient in the FOV of the plurality of SPECT imaging detectors. As an illustration, referring to FIGS. 2L and 3, example operations at 303 can include selective translational movement of the FIG. 2L bed structure 234, along the linear axis 211. As described above, example operations to effectuate such movement along the linear axis 211 can include rotation of the bed motor 237, and translation of that rotation by the bed ball screw mechanism 238 to linear movement of the sliding member 240 along the two linear guide bars 239. With continuing reference to FIG. 3, upon completion of operations at 303, the flow 300 can proceed to 304 and apply operations of moving the plurality of SPECT imaging detectors around and near the patient's body using the robotic arm, concurrent with moving, if necessary, the patient along the linear axis, to maintain a region of interest of the patient's body in alignment with the FOV of the SPECT imaging detectors. Example operations at 304 can include the can include the selective translational movement of the FIG. 2L bed structure 234, along the linear axis 211, as described above.

EXAMPLE

A phantom study phantom study is used to evaluate the performance of the robotic SPECT imaging system of the present application. A cardiac phantom is used in the SPECT imaging process performed by the robotic system of the present disclosure. The user interface unit is used to define the SPECT imaging parameters, which include the angle of roll-rotation movement of the head assembly along the first roll axis. To perform a full scan from the left posterior oblique to the right anterior oblique, the head assembly should roll, for example, 90 degrees along the first roll axis. The distance between the SPECT imaging detectors and the patient's body can be set using the user interface unit, as well. A scan radius of, for example, 30 cm is set using the user interface unit. The sensor system sends the data regarding the current position of the robotic arm and the patient support assembly to the controller. The controller calculates the position and the motion of the robotic arm and the patient support assembly based on the data received from the user interface unit and the data received from the sensor system. In this example, in order to perform a 90° scan from the left posterior oblique to the right anterior oblique, with a radius or distance of about 30 cm from the patient's body, the head assembly rotates 10 degrees along the third roll axis, the second arm rotates 10 degrees along the second roll axis and the first arm assembly rotates 90 degrees along the first roll axis.

Two SPECT imaging detectors are placed inside the detector housings attached to the head assembly. Technetium-99m is a radiopharmaceutical, which is injected to the patient before the SPECT imaging. The major components of the SPECT imaging detector include: a collimator, which is a lead plate that contains a large number of holes and is used to define the direction of the detected gamma rays; a large area scintillation crystal; a light guide; and an array of photomultiplier tubes (PMTs), which are coupled optically to the back face of the crystal and arranged in a hexagonal pattern to maximize the area of the scintillation crystal.

Figure 4:
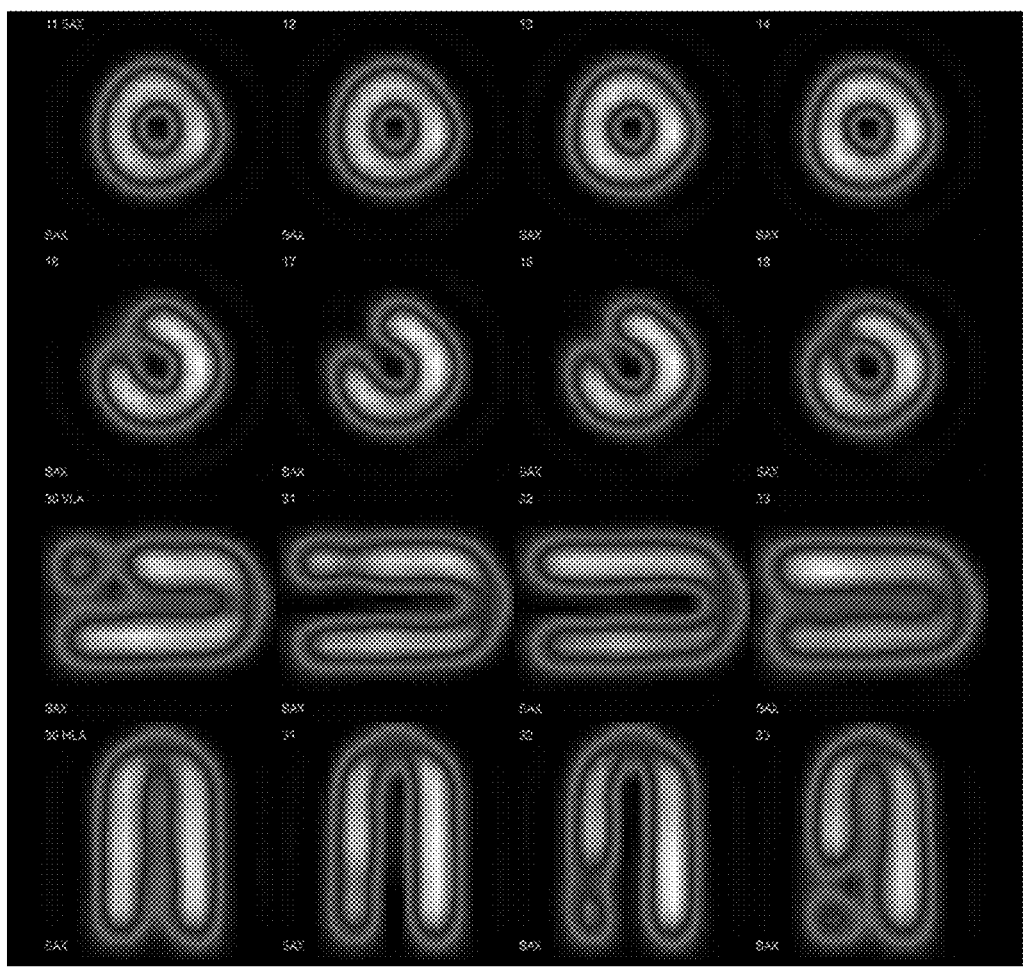
FIG. 4 illustrates example SPECT images obtained using a robotic assembly according to one or more aspects of the present application.

FIG. 4 illustrates images of the cardiac phantom obtained by the SPECT imaging system of the present disclosure. In this example, each SPECT imaging detector includes a rectangular NaI(Tl) crystal, which is capable of transforming the incoming 140 keV photons, resulted from the gamma decay of Technetium-99m, into visible light. The visible light is then increased by 24 PMTs to be accurately measured. Each NaI(Tl) crystal has an area of 40×25 $mm^2$ area and a thickness of 9.5 mm. The crystal is followed by 18 mm fused-quartz light-guide. An array of 24 rectangular PMTs in 4×6 form is coupled optically to the back face of the crystal with a silicone-based adhesive. This adhesive has suitable transparency and adherence, and it is useful to remove air bubbles that can degrade the image quality. As can be seen in FIG. 4, high quality images of the cardiac phantom can be obtained utilizing the robotic system of the present application. The quality of the images is due to the small distance between the detectors and the patient's body.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 105 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations for the purpose of streamlining the disclosure. This method of disclosure is not to be interpreted as reflecting an intention that the claimed implementations require more features than are expressly recited in each claim. Rather, as the following claims reflect, inventive subject matter lies in less than all features of a single disclosed implementation. Thus the following claims are hereby incorporated into the Detailed Description, with each claim standing on its own as a separately claimed subject matter.

What is claimed is:

1. An apparatus for single photon emission computed tomography (SPECT) imaging, comprising:
    a robotic arm movable in three rotational degrees of freedom, the three rotational degrees of freedom comprise a first roll axis, a second roll axis and a third roll axis, the robotic arm including:
        a base end and a distal end, the distal end configured to support a plurality of SPECT imaging detectors;
        a first arm assembly having a first rotational mechanism coupled with a proximal end of a second arm, the first rotational mechanism configured to drive a roll-rotation movement of the second arm along the second roll axis;
        a head assembly configured to house the plurality of SPECT imaging detectors, the head assembly being attached to the distal end of the second arm, the head assembly including a head rotational mechanism configured to drive a roll-rotation movement of the head assembly along the third roll axis;
        and
        a base assembly having a base rotational mechanism coupled with the first arm assembly, the base rotational mechanism configured to drive a roll-rotation movement of the first arm assembly along the first roll axis;
    a patient support assembly movable in a linear degree of freedom; and
    a controller configured to cause the robotic arm to move the plurality of SPECT imaging detectors in three dimensions around a patient's body to obtain SPECT images, and cause the patient support assembly to move along the linear degree of freedom to maintain alignment of the patient's body with the plurality of SPECT imaging detectors.

2. The apparatus of claim 1, wherein the head assembly includes a plurality of detector housings, the plurality of detector housings being configured to hold the plurality of SEPCT imaging detectors.

3. The apparatus of claim 1, wherein the roll-rotation movement of the second arm along the second roll axis is in a rotational range of about 70 degrees.

4. The apparatus of claim 1, wherein the roll-rotation of the head assembly along the third roll axis is in a rotational range of about 50 degrees.

5. The apparatus of claim 1, wherein the base rotational mechanism includes a base motor coupled to a base shaft, the base motor and the base shaft being configured to drive the roll-rotation movement of the first arm assembly along the first roll axis.

6. The apparatus of claim 1, wherein the first rotational mechanism includes a first motor coupled to a first shaft, the first motor and the first shaft being configured to drive the roll-rotation movement of the second arm along the second roll axis.

7. The apparatus of claim 1, wherein the head rotational mechanism includes a head motor coupled to a head shaft, the head motor and the head shaft being configured to drive the roll-rotation movement of the head assembly along the third roll axis.

8. The apparatus of claim 1, wherein the first roll axis, the second roll axis, the third roll axis are parallel.

9. The apparatus of claim 8, wherein the degree of linear freedom is along a linear axis, and wherein the linear axis is parallel to the first roll axis, the second roll axis, and the third roll axis.

10. The apparatus of claim 1, wherein the base rotational mechanism further includes:
a base motor coupled to a base shaft; and
an encoder coupled to the base rotational mechanism and configured to detect the position and movement of the base shaft along the first roll axis, and to send to the controller the detected position and movement of the base shaft along the first roll axis.

11. The apparatus of claim 1, wherein the first rotational mechanism further includes:
a first motor coupled to a first shaft; and
an absolute encoder coupled to the first rotational mechanism and configured to detect the position and movement of the first shaft along the second roll axis.

12. The apparatus of claim 1, wherein the head rotational mechanism further includes:
a head motor coupled to a head shaft; and
an absolute encoder coupled to the head rotational mechanism and configured to detect the position and movement of the head shaft along the third roll axis, and to send to the controller the detected position and movement of the head shaft along the first roll axis.

13. The apparatus of claim 12, wherein the patient support assembly comprises a bed having a bed structure and, supported on the bed structure, a bed pad.

14. The apparatus of claim 1, wherein
the first rotational mechanism further configured to rotate the plurality of SPECT imaging detectors around the patient's body at a given distance, wherein the plurality of SPECT imaging detectors are configured to be rotatable around the patient's body in a roll-rotation movement from a left posterior oblique to a right anterior oblique in a given rotational range.

15. The apparatus of claim 14, wherein the rotational range is approximately 90 degrees, and wherein the distance is in a range of about 18 to 48 centimeters.

16. A method for single photon emission computed tomography (SPECT) imaging, comprising:
positioning a patient on a patient support that is movable along a linear axis;
rotating a first arm in a rotation along a first roll axis, the first roll axis extending through a proximal end of the first arm;
rotating a second arm in a rotation along a second roll axis, the second roll axis extending parallel to the linear axis and extending through a distal end of the first arm and a proximal end of the second arm, and being parallel to the first roll axis;
rotating a plurality of SPECT imaging detectors, located at a distal end of the second arm, about a third roll axis, the third roll axis being parallel to the first roll axis; and
moving the patient support in the linear degree of motion, in a manner maintaining alignment of a selected region on the patient's body with a field of view (FOV) of the plurality of SPECT imaging detectors.

* * * * *